(12) United States Patent
Grey

(10) Patent No.: US 6,759,541 B2
(45) Date of Patent: Jul. 6, 2004

(54) EPOXIDATION PROCESS USING A SUPPORTED NIOBIUM OXIDE CATALYST

(75) Inventor: Roger A. Grey, West Chester, PA (US)

(73) Assignee: ARCO Chemical Technology, L.P., Greenville, DE (US)

( * ) Notice: Subject to any disclaimer, the term of this patent is extended or adjusted under 35 U.S.C. 154(b) by 33 days.

(21) Appl. No.: 10/161,002

(22) Filed: Jun. 3, 2002

(65) Prior Publication Data
US 2003/0225293 A1 Dec. 4, 2003

(51) Int. Cl.$^7$ ............................................. C07D 301/12
(52) U.S. Cl. ...................................................... 549/531
(58) Field of Search ........................................ 549/531

(56) References Cited

U.S. PATENT DOCUMENTS

| | | | |
|---|---|---|---|
| 3,166,542 A | 1/1965 | Orzechowski et al. | 260/93.7 |
| 3,351,635 A | 11/1967 | Kollar | 260/348.5 |
| 3,829,392 A | 8/1974 | Wulff | 252/430 |
| 3,923,843 A | 12/1975 | Wulff | 260/348.5 L |
| 4,367,342 A | 1/1983 | Wulff et al. | 549/529 |
| 4,833,260 A | 5/1989 | Neri et al. | 549/531 |
| 5,679,749 A | 10/1997 | Saxton et al. | 525/360 |
| 5,859,265 A | 1/1999 | Müller et al. | 549/531 |

FOREIGN PATENT DOCUMENTS

| | | |
|---|---|---|
| JP | 4-352771 | 12/1992 |
| WO | WO 98/00413 | 1/1998 |

Primary Examiner—Taofiq Solola
(74) Attorney, Agent, or Firm—Kevin M. Carroll

(57) ABSTRACT

The invention is a liquid-phase process for epoxidizing olefins with hydrogen peroxide in the presence of a non-zeolitic, supported niobium oxide catalyst comprising niobium oxide and a support. The process exhibits good productivity and selectivity for olefin epoxidation with hydrogen peroxide.

18 Claims, No Drawings

EPOXIDATION PROCESS USING A SUPPORTED NIOBIUM OXIDE CATALYST

FIELD OF THE INVENTION

This invention relates to a liquid-phase epoxidation process using a non-zeolitic, supported niobium oxide catalyst to produce epoxides from hydrogen peroxide and olefins. Surprisingly, the supported niobium oxide catalyst is active in liquid-phase epoxidation.

BACKGROUND OF THE INVENTION

Many different methods for the preparation of epoxides have been developed. Generally, epoxides are formed by the reaction of an olefin with an oxidizing agent in the presence of a catalyst. The production of propylene oxide from propylene and an organic hydroperoxide, such as ethyl benzene hydroperoxide or tert-butyl hydroperoxide, is commercially practiced technology. This process is performed in the presence of a solubilized molybdenum catalyst, see U.S. Pat. No. 3,351,635, or a heterogeneous titania on silica catalyst, see U.S. Pat. No. 4,367,342. Another commercially practiced technology is the direct epoxidation of ethylene to ethylene oxide by reaction with oxygen over a silver catalyst.

Much current research is conducted in the direct epoxidation of olefins with oxygen and hydrogen. For example, JP 4-352771 discloses the formation of propylene oxide from propylene, oxygen, and hydrogen using a catalyst containing a Group VIII metal such as palladium on a crystalline titanosilicate. The Group VIII metal is believed to promote the reaction of oxygen and hydrogen to form an in situ oxidizing agent. U.S. Pat. No. 5,859,265 discloses a catalyst in which a platinum metal, selected from Ru, Rh, Pd, Os, Ir and Pt, is supported on a titanium or vanadium silicalite. Other direct epoxidation catalyst examples include gold supported on titanosilicates, see for example PCT Intl. Appl. WO 98/00413.

Besides oxygen and alkyl hydroperoxides, another oxidizing agent useful for the preparation of epoxides is hydrogen peroxide. U.S. Pat. No. 4,833,260, for example, discloses olefin epoxidation using hydrogen peroxide and a titanium silicate zeolite. U.S. Pat. No. 5,679,749 discloses the epoxidation of olefins with hydrogen peroxide in the presence of a crystalline siliceous molecular sieve zeolite wherein niobium is isomorphously substituted for silica in the framework. One drawback of these processes is the expense of the titanium and niobium zeolites.

In sum, new processes for the epoxidation of olefins using hydrogen peroxide are needed. I have discovered an effective, convenient epoxidation process that gives good productivity and selectivity to epoxide.

SUMMARY OF THE INVENTION

The invention is an olefin epoxidation process that comprises reacting an olefin and hydrogen peroxide in a solvent in the presence of a non-zeolitic, supported niobium oxide catalyst. The supported niobium oxide catalyst is surprisingly useful in the epoxidation of olefins with hydrogen peroxide.

DETAILED DESCRIPTION OF THE INVENTION

The process of the invention employs a non-zeolitic, supported niobium oxide catalyst. The supported niobium oxide catalyst comprises niobium oxide and a support. The amount of niobium contained in the supported niobium oxide catalyst can be varied, but generally the catalyst composition contains, based on total catalyst composition, at least 0.01% by weight of niobium with amounts from about 0.01% by weight to about 50% by weight being preferred and amounts from about 0.1% to about 15% by weight being most preferred.

The support can be inorganic oxides, inorganic chlorides, carbon, or mixtures thereof. Preferred inorganic oxides include oxides of Group 2, 3, 4, 5, 13, or 14 elements as well as refractory oxides such as silica-alumina, silica-magnesia, silica-titania, silica-zirconia, silica-alumina-boric, magnesia-alumina, and silica-alumina-magnesia. Preferred inorganic chlorides include chlorides of the Group 2 elements. Particularly preferred supports include silica, alumina, silica-aluminas, sodium aluminum silicate, magnesias, titania, zirconia, silica-titanias, tantalum oxides, mordenite, hydrotalcites, magnesium chloride, and carbon. Most preferred are supports that consist essentially of pure silica, e.g., materials containing at least 90% silica.

Preferably, the support has a surface area in the range of about 10 to about 700 $m^2/g$, more preferably from about 50 to about 500 $m^2/g$, and most preferably from about 100 to about 400 $m^2/g$. Preferably, the pore volume of the support is in the range of about 0.1 to about 4.0 mL/g, more preferably from about 0.5 to about 3.5 mL/g, and most preferably from about 0.8 to about 3.0 mL/g. Preferably, the average particle size of the support is in the range of about 10 to about 500 $\mu m$, more preferably from about 20 to about 200 $\mu m$, and most preferably from about 10 to about 100 $\mu m$. The average pore diameter is typically in the range of about 10 to about 1000 Å, preferably about 20 to about 500 Å, and most preferably about 50 to about 350 Å.

The term non-zeolitic is meant to exclude zeolite and zeolite-like structures. Zeolite and zeolite-like structures include crystalline siliceous molecular sieve zeolite wherein niobium is isomorphously substituted for silica in the framework such as those described in U.S. Pat. No. 5,679,749.

The preparation of the supported niobium oxide catalyst may be accomplished by a variety of techniques known in the art. One such method involves impregnating a support with a niobium compound (e.g., Nb(OEt)$_5$), optionally followed by drying. The niobium compounds include any suitable niobium halide (such as NbCl$_5$ and NbBr$_5$), niobium alkoxide (such as Nb(OEt)$_5$), or niobium halide alkoxides (such as NbCl$_3$(OEt)$_2$). In another technique, the catalyst composition is suitably prepared by calcining a mixture of the support and a niobium oxide at an elevated temperature, e.g., 500° C. to 1000° C. Alternatively, the catalyst composition is prepared by cogelling a mixture of a niobium salt and a silica sol by conventional methods of preparing metal supported catalyst compositions. In still another technique, the catalyst composition is prepared by the surface reaction of silanol groups of an inorganic siliceous solid with a niobium salt by the procedure disclosed in U.S. Pat. No. 3,166,542. In yet another technique, a catalyst composition comprising a fumed, pyrogenic niobia-silica is prepared by the combustion of hydrogen and oxygen with a mixture of silicon tetrahalide and niobium halide in accordance with conventional methods of preparing finely-divided fumed metal oxides and silica. Other techniques for incorporating an oxide or hydroxide of niobium on a support such as dry-mixing, co-precipitation, impregnation and ion-exchange are also suitably employed.

One class of catalysts particularly suitable for the epoxidation of olefins is niobia-on-silica (also sometimes referred to as "Nb$_2$O$_5$/SiO$_2$"), which comprises niobia (niobium (V) oxide) supported on silica (silicon dioxide). The niobia-on-silica catalyst may be silylated after thermal treatment and prior to use. The catalyst is silylated by treatment with an organic silylating agent at elevated temperature. Silylation is preferably performed after calcination and most preferably after both calcination and reaction with water. Suitable silylation methods adaptable for use in the present invention are described in U.S. Pat. Nos. 3,829,392 and 3,923,843 (incorporated hereby by reference in their entirety). Suitable silylating agents include organosilanes, organohalosilanes, and organodisilazanes.

After catalyst formation, the supported niobium oxide catalyst may be optionally thermally treated in a gas such as nitrogen, helium, vacuum, hydrogen, oxygen, air, or the like. The thermal treatment temperature is typically from about 100 to about 1000° C., preferably from about 200 to about 800° C.

The supported niobium oxide catalyst may be used in the epoxidation process as a powder or as a pellet. If pelletized or extruded, the catalyst may additionally comprise a binder or the like and may be molded, spray dried, shaped or extruded into any desired form prior to use in epoxidation.

The epoxidation process of the invention comprises contacting an olefin and hydrogen peroxide in the presence of the supported niobium oxide catalyst in a solvent. Suitable olefins include any olefin having at least one carbon-carbon double bond, and generally from 2 to 60 carbon atoms. Preferably the olefin is an acyclic alkene of from 2 to 30 carbon atoms; the process of the invention is particularly suitable for epoxidizing $C_2$–$C_6$ olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro groups, or the like. The process of the invention is especially useful for converting propylene to propylene oxide.

The hydrogen peroxide is generated prior to use in the epoxidation reaction. Hydrogen peroxide may be derived from any suitable source, including oxidation of secondary alcohols such as isopropanol, the anthraquinone process, and from direct reaction of hydrogen and oxygen. The concentration of the aqueous hydrogen peroxide reactant added into the epoxidation reaction is not critical. Typical hydrogen peroxide concentrations range from 0.1 to 90 weight percent hydrogen peroxide in water, preferably 1 to 5 weight percent.

The amount of hydrogen peroxide to the amount of olefin is not critical, but most suitably the molar ratio of hydrogen peroxide:olefin is from 100:1 to 1:100, and more preferably in the range of 10:1 to 1:10. One equivalent of hydrogen peroxide is theoretically required to oxidize one equivalent of a mono-unsaturated olefin substrate, but it may be desirable to employ an excess of one reactant to optimize selectivity to the epoxide.

The process of the invention also requires the use of a solvent. Suitable solvents include any chemical that is a liquid under reaction conditions, including, but not limited to, oxygen-containing hydrocarbons such as alcohols, aromatic and aliphatic solvents such as toluene and hexane, chlorinated aromatic and aliphatic solvents such as methylene chloride and chlorobenzene, and water. Preferred solvents are oxygenated solvents that contain at least one oxygen atom in its chemical structure. Suitable oxygenated solvents include water and oxygen-containing hydrocarbons such as alcohols, ethers, esters, ketones, and the like. Preferred oxygenated solvents include lower aliphatic $C_1$–$C_4$ alcohols such as methanol, ethanol, isopropanol, and tert-butanol, or mixtures thereof, and water. Fluorinated alcohols can be used. It is also possible to use mixtures of the cited alcohols with water. A particularly preferred solvent is methanol or a mixture of methanol and water.

The process of the invention may be carried out in a batch, continuous, or semi-continuous manner using any appropriate type of reaction vessel or apparatus such as a fixed-bed, transport bed, fluidized bed, stirred slurry, or CSTR reactor. The catalyst is preferably in the form of a suspension or fixed-bed. Known methods for conducting metal-catalyzed epoxidations of olefins using an oxidizing agent will generally also be suitable for use in this process. Thus, the reactants may be combined all at once or sequentially.

Epoxidation according to the invention is carried out at a temperature effective to achieve the desired olefin epoxidation, preferably at temperatures in the range of 0–150° C., more preferably, 20–120° C. Reaction or residence times of from about 1 minute to 48 hours, more preferably 1 minute to 8 hours will typically be appropriate. It is advantageous to work at a pressure of 1 to 100 atmospheres, although the reaction can also be performed at atmospheric pressure.

The amount of supported niobium oxide catalyst used may be determined on the basis of the molar ratio of the niobium contained in the catalyst to the olefin that is supplied per unit time. Typically, sufficient catalyst is present to provide a niobium/olefin per hour molar feed ratio of from 0.0001 to 0.1.

The following examples merely illustrate the invention. Those skilled in the art will recognize many variations that are within the spirit of the invention and scope of the claims.

EXAMPLE 1

Preparation of Niobium Oxide on Silica Catalysts

Catalysts 1A, 1B, and 1C: 1.4 Weight Percent Niobium

Catalyst 1A: Silica (20 g, Davidson 952) is slurried in 60 grams of methanol. Niobium (V) ethoxide (1.2 g dissolved in 10 g of methanol) is added to the silica slurry over a 10-minute period with stirring. The mixture is stirred for 18 hours at room temperature, filtered, and the solids washed are with 50 mL of methanol. The solids are dried at 110° C. for 2 hours to give 20.9 grams. The solids analyzed for 1.37 wt. % niobium.

Catalyst 1B: Catalyst 1A (5 g) is calcined under 4 volume % oxygen in nitrogen at 450° C. for 4 hours.

Catalyst 1C: Catalyst 1B is then calcined under 4 volume % oxygen in nitrogen at 550° C. for 4 hours.

Catalysts 1D and 1E: 11 Weight Percent Niobium

Catalyst 1D is prepared according to the procedure of Catalyst 1A, except that 10 grams of niobium (V) ethoxide in 50 grams of methanol is used. Elemental analysis shows 11 wt. % niobium.

Catalyst 1E is produced by calcining Catalyst 1D (5 g) under 4 volume % oxygen in nitrogen at 450° C. for 4 hours.

EXAMPLE 2

Preparation of Niobia-Titania on Silica Catalysts

Catalyst 2 is prepared by slurrying Davidson 952 silica (20 g) in 60 grams of methanol. Niobium (V) ethoxide (5 g) and titanium (IV) isopropoxide (1 g) are dissolved in 10 grams of methanol and added to the silica slurry over a 10-minute period with stirring. The slurry is stirred at 23° C. for 18 hours, filtered, and the solids are washed with 50 mL of methanol. The solids are dried at 110° C. for 2 hours to give 20.4 grams. Elemental analysis shows 5.4 wt. % niobium and 0.74 wt. % titanium.

The dried solids (5 grams) are calcined under 4 volume % oxygen in nitrogen at 450° C. for 4 hours.

Comparative Example 3

Preparative of Niobic Acid

Niobium (V) ethoxide (50 g) is dissolved in 50 grams of methanol and added to 200 grams of deionized water. The reaction mixture is cooled in an ice bath over a 20-minute period, then stirred at 23° C. for 2 hours. The solids are filtered, washed once with a mixture of water (40 grams) and methanol (10 mL) and once with 50 mL of methanol. The solids are dried in a vacuum oven (0.5 torr) at 50° C. for 2 hours, and finally at 110° C. for 5 hours to give 24 grams of Comparative Catalyst 3. The solids-analyzed for 69.8 wt. % niobium.

Comparative Example 4

Niobium Oxide

Niobium oxide is a product of Reference Metals. Elemental analysis shows niobium =67 wt. %.

Comparative Example 5

Preparation of Tantalum Oxide on Silica Catalysts

Comparative Catalyst 5 is prepared by slurrying Davidson 952 silica (20 g) in 60 grams of methanol. Tantalum (V) ethoxide (2 g, dissolved in 10 g of methanol) is added to the silica slurry over a 10-minute period with stirring. The slurry is stirred at 23° C. for 18 hours, filtered, and the solids are washed with 50 mL of methanol. The solids are dried at 110° C. for 2 hours to give 20.9 grams. Elemental analysis shows 4.3 wt. % tantalum.

The dried solids (5 g) are calcined under 4 volume % oxygen in nitrogen at 450° C. for 4 hours.

EXAMPLE 6

Propylene Epoxidation Reactions

Catalysts 1A, 1B, 1C, 1D, 1E, and 2 and Comparative Catalysts 3, 4, and 5 are tested in propylene epoxidation according to the following procedure.

A 100-mL Parr reactor equipped with a magnetic stir bar is charged with 40 grams of a methanol/water/hydrogen peroxide solution (70% methanol, 25% water and 5 % hydrogen peroxide by weight) and 150 mg of catalyst. The reactor is closed, charged with propylene (17 g), and heated at 50° C. for 30 minutes (except for runs with catalysts 1B and 2, which were for 2 hours) while stirring with the magnetic stir bar. The reactor is then cooled to 10° C. and the propylene vented into a gas bag. The liquid and gas phases are analyzed by GC.

The results and the reaction temperature are shown in Table 1.

The epoxidation results show that the use of a supported niobium oxide catalyst surprisingly leads to the production of propylene oxide (PO) in high selectivity. The propylene oxide yield is significantly higher for the supported niobium oxide catalysts compared to unsupported niobic acid, unsupported niobium oxide, and supported tantalum oxide catalysts.

TABLE 1

| Catalyst # | Epoxidation Results | | |
|---|---|---|---|
|  | PO Yield (mmol) | PG Yield (mmol) | PM Ethers Yield (mmol) |
| 1A | 3.73 | 0.06 | 0.33 |
| 1B | 7.3 | 0.02 | 0.53 |
| 1C | 3.43 | 0 | 0.11 |
| 1D | 4 | 0.22 | 0.24 |
| 1E | 4.9 | 0.07 | 0.32 |
| 2 | 2.84 | 0.04 | 0.37 |
| 3* | 1.9 | 0.41 | 1.05 |
| 4* | 1.7 | 0 | 0.22 |
| 5* | 0.36 | — | — |

*Comparative Example

I claim:

1. A process for producing an epoxide comprising reacting an olefin and hydrogen peroxide in a solvent in the presence of a non-zeolitic, supported niobium oxide catalyst comprising niobium oxide and a support.

2. The process of claim 1 wherein the supported niobium oxide catalyst is comprised of from 0.01 to 50 weight percent niobium.

3. The process of claim 1 wherein the support is selected from the group consisting of inorganic oxides, inorganic chlorides, and carbon.

4. The process of claim 3 wherein the support is selected from the group consisting of silica, alumina, silica-aluminas, sodium aluminum silicate, magnesias, titania, zirconia, silica-titanias, tantalum oxides, mordenite, magnesium chloride, and carbon.

5. The process of claim 3 wherein the support is silica.

6. The process of claim 1 wherein the olefin is a $C_2$–$C_6$ olefin.

7. The process of claim 6 wherein the olefin is propylene.

8. The process of claim 1 wherein the solvent comprises an oxygenated solvent selected from the group consisting of alcohols, ethers, esters, ketones, water, and mixtures thereof.

9. The process of claim 7 wherein the solvent is selected from the group consisting of water, $C_1$–$C_4$ alcohols, and mixtures thereof.

10. The process of claim 1 wherein the solvent comprises methanol.

11. The process of claim 1 wherein the molar ratio of hydrogen peroxide to olefin is in the range of from about 10:1 to about 1:10.

12. The process of claim 1 wherein the process is performed at a temperature from about 20° C. to about 120° C.

13. The process of claim 1 wherein the non-zeolitic, supported niobium oxide catalyst is produced by:
   (a) impregnating the support with a niobium compound; and
   (b) calcining the impregnated product of step (a) at a temperature of at least 100° C. in the presence of a gas stream comprised of oxygen to form the supported niobium oxide catalyst.

14. The process of claim 13 wherein the niobium compound is selected from the group consisting of niobium alkoxides and niobium halides.

15. A process for producing propylene oxide comprising reacting propylene and hydrogen peroxide in an oxygenated solvent in the presence of a non-zeolitic, supported niobium oxide catalyst comprising niobium oxide and silica.

16. The process of claim 15 wherein the supported niobium oxide catalyst is comprised of from 0.01 to 50 weight percent niobium.

17. The process of claim 15 wherein the oxygenated solvent is an oxygenated solvent selected from the group consisting of water, $C_1$–$C_4$ alcohols, and mixtures thereof.

18. The process of claim 17 wherein the solvent is methanol.

* * * * *